US010299822B1

(12) United States Patent
Huddleston

(10) Patent No.: US 10,299,822 B1
(45) Date of Patent: *May 28, 2019

(54) DOUBLE BLADED SURGICAL TOOL IN COMBINATION WITH A TARGETING GUIDE

(71) Applicant: Herbert D. Huddleston, Tarzana, CA (US)

(72) Inventor: Herbert D. Huddleston, Tarzana, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/282,935

(22) Filed: Sep. 30, 2016

Related U.S. Application Data

(62) Division of application No. 14/727,715, filed on Jun. 1, 2015, now Pat. No. 9,456,840, and a division of application No. 13/461,460, filed on May 1, 2012, now Pat. No. 9,089,357.

(51) Int. Cl.
*A61B 17/3201* (2006.01)
*A61B 17/3211* (2006.01)
*A61B 17/72* (2006.01)
*A61B 17/00* (2006.01)
A61B 17/32 (2006.01)

(52) U.S. Cl.
CPC .... *A61B 17/3201* (2013.01); *A61B 17/00234* (2013.01); *A61B 17/3211* (2013.01); *A61B 17/725* (2013.01); A61B 2017/320052 (2013.01)

(58) Field of Classification Search
CPC ......... A61B 17/00; A61B 17/02; A61B 17/32; A61B 17/3201; A61B 17/3209; A61B 17/3211; A61B 19/00; B26B 13/00

USPC ........ 30/152, 299, 304, 232, 227, 237, 244, 30/245, 260; 606/167, 170, 172, 174, 606/205, 39, 79; 600/564; 433/144

See application file for complete search history.

(56) References Cited

U.S. PATENT DOCUMENTS

| 253,359 | A | * | 2/1882 | Ewing | A61B 17/3201 |
| | | | | | 606/174 |
| 487,068 | A | * | 11/1892 | Drinkwater et al. | A61N 1/056 |
| | | | | | 30/245 |
| 681,327 | A | * | 8/1901 | Klever, Jr. | A41H 25/02 |
| | | | | | 606/174 |
| 858,003 | A | * | 6/1907 | Klever | B25F 1/003 |
| | | | | | 606/174 |
| 1,301,753 | A | * | 4/1919 | Seniw | F41C 9/085 |
| | | | | | 30/232 |
| 1,348,194 | A | * | 8/1920 | Wescott | A22B 5/04 |
| | | | | | 30/272.1 |
| 1,771,031 | A | * | 7/1930 | Court | B26B 11/005 |
| | | | | | 30/146 |

(Continued)

FOREIGN PATENT DOCUMENTS

WO    WO 2013172998 A4 *  3/2014  ......... A61B 17/3211

*Primary Examiner* — Jason Daniel Prone
(74) *Attorney, Agent, or Firm* — Thomas I. Rozsa

(57) ABSTRACT

An apparatus for creating minimal skin incisions and soft tissue tunnels, particularly useful in the insertion of transverse or oblique screws through a bone and the holes in a locking nail embedded within the intra-medullary cavity of the bone. A unique surgical tool, as described herein, is used in conjunction with a targeting guide and targeting guide tunnel to create skin and soft-tissue tunnels that are precise, of minimal size, and minimally traumatic for the patient, and very quick and easy for the surgeon to create and to repair.

1 Claim, 15 Drawing Sheets

(56) References Cited

U.S. PATENT DOCUMENTS

| | | | | |
|---|---|---|---|---|
| 2,069,636 A * | 2/1937 | Wilson | A61B 17/3201 | 606/174 |
| 2,674,796 A * | 4/1954 | Herold | H02G 1/1214 | 30/262 |
| 4,255,854 A * | 3/1981 | Bilbao | A47J 17/04 | 30/304 |
| 4,394,864 A * | 7/1983 | Sandhaus | A61F 6/204 | 606/157 |
| 4,601,710 A * | 7/1986 | Moll | A61B 17/3496 | 30/152 |
| 4,674,501 A * | 6/1987 | Greenberg | A61B 17/32001 | 606/174 |
| 4,712,545 A * | 12/1987 | Honkanen | A61B 17/1608 | 606/184 |
| 4,783,867 A * | 11/1988 | Tsao | B26B 11/005 | 30/123 |
| 4,887,612 A * | 12/1989 | Esser | A61B 10/06 | 606/174 |
| 5,100,391 A * | 3/1992 | Schutte | A61B 17/3213 | 30/304 |
| 5,100,420 A * | 3/1992 | Green | A61B 17/1285 | 606/143 |
| 5,192,298 A * | 3/1993 | Smith | A61B 10/06 | 606/174 |
| 5,201,752 A * | 4/1993 | Brown | A61B 17/29 | 606/170 |
| 5,211,655 A * | 5/1993 | Hasson | A61B 17/2909 | 606/170 |
| 5,255,438 A * | 10/1993 | Morgan | B26B 11/005 | 30/244 |
| 5,275,613 A * | 1/1994 | Haber | A61B 17/29 | 606/205 |
| 5,282,806 A * | 2/1994 | Haber | A61B 17/29 | 606/205 |
| 5,358,508 A * | 10/1994 | Cobb | A61B 17/29 | 606/170 |
| 5,368,606 A * | 11/1994 | Marlow | A61B 17/29 | 606/170 |
| 5,391,166 A * | 2/1995 | Eggers | A61B 18/12 | 606/170 |
| 5,447,516 A * | 9/1995 | Gardner | A61B 17/3213 | 606/167 |
| 5,452,514 A * | 9/1995 | Enfaradi | B26B 27/00 | 30/299 |
| 5,486,189 A * | 1/1996 | Mudry | A61B 17/29 | 606/167 |
| 5,620,456 A * | 4/1997 | Sauer | A61B 17/3417 | 606/170 |
| 5,674,237 A * | 10/1997 | Ott | A61B 17/3496 | 606/167 |
| 5,676,679 A * | 10/1997 | Simon | A61F 9/00781 | 606/107 |
| 5,752,972 A * | 5/1998 | Hoogeboom | A61B 17/29 | 606/174 |
| 5,779,727 A * | 7/1998 | Orejola | A61B 17/320016 | 606/174 |
| 5,810,879 A * | 9/1998 | de Guillebon | A61B 17/29 | 606/174 |
| 5,893,874 A * | 4/1999 | Bourque | A61B 17/29 | 606/170 |
| 5,893,875 A * | 4/1999 | O'Connor | A61B 17/29 | 606/167 |
| 6,007,561 A * | 12/1999 | Bourque | A61B 17/29 | 606/170 |
| 6,168,605 B1 * | 1/2001 | Measamer | A61B 17/320016 | 606/170 |
| 6,488,693 B2 * | 12/2002 | Gannoe | A61B 17/320016 | 606/170 |
| 6,698,099 B2 * | 3/2004 | Ronan | B26B 1/02 | 30/254 |
| 7,122,028 B2 * | 10/2006 | Looper | A61B 17/320016 | 606/205 |
| 7,131,982 B1 * | 11/2006 | Karapetyan | A61B 17/3213 | 606/167 |
| 7,578,832 B2 * | 8/2009 | Johnson | A61B 17/1608 | 606/174 |
| 8,037,591 B2 * | 10/2011 | Spivey | A61B 17/320016 | 606/174 |
| 8,114,120 B2 * | 2/2012 | Johnson | A61B 17/1608 | 606/174 |
| 8,333,780 B1 * | 12/2012 | Pedros | A61B 17/29 | 606/174 |
| 9,089,357 B2 * | 7/2015 | Huddleston | A61B 17/3211 | 30/299 |
| 9,456,840 B1 * | 10/2016 | Huddleston | A61B 17/3211 | 30/299 |
| 2006/0241665 A1 * | 10/2006 | Bosley | A61B 17/320016 | 606/167 |
| 2007/0149893 A1 * | 6/2007 | Heske | A61B 10/0275 | 606/167 |
| 2009/0216258 A1 * | 8/2009 | Geuder | A61B 17/3211 | 606/170 |
| 2010/0121367 A1 * | 5/2010 | Lin | A61B 17/2909 | 606/174 |
| 2011/0022052 A1 * | 1/2011 | Jorgensen | A61B 17/1611 | 606/174 |
| 2012/0078282 A1 * | 3/2012 | Livneh | A61B 17/320016 | 606/174 |
| 2012/0184809 A1 * | 7/2012 | Bleich | A61B 17/1659 | 600/104 |
| 2013/0218159 A1 * | 8/2013 | Kappel | A61B 17/29 | 606/167 |
| 2013/0274776 A1 * | 10/2013 | Begg | A61B 17/3494 | 606/172 |

* cited by examiner

DOUBLE BLADED SURGICAL TOOL IN COMBINATION WITH A TARGETING GUIDE

This patent application is a divisional of application Ser. No. 14/727,715 filed on Jun. 1, 2015, now issued on Oct. 4, 2016 as U.S. Pat. No. 9,456,840 B1, and which was a divisional of application Ser. No. 13/461,460 filed on May 1, 2012, now issued on Jul. 28, 2015 as U.S. Pat. No. 9,089,357.

BACKGROUND OF THE INVENTION

1. Field of the Invention

The present invention relates to the field of orthopedic surgery and in particular to making incisions in the skin and soft tissues to go directly to the surface of a fractured bone to affix locking screws into the bone. The present invention further relates to the use of a locking nail and guide means to reach to the surface of the bone so that a proper incision can be made to enable a locking screw to be affixed into the bone and the embedded locking nail with a minimum of surgical cutting and blood loss. The present invention also relates to the field of scalpels used to make the required incision so that a locking screw can be affixed into the bone with a minimum of surgical cutting and blood loss.

2. Description of the Prior Art

The fairly recent development of intra-medullary locking nails has been a significant breakthrough in the surgical management of fractures of the long bones in humans and animals.

Locking nails provide superior fixation to that provided by on-lay plates secured by screws. Equally significantly, they can be installed in the bone with far less surgical injury to the patient. The skin incisions are smaller. The soft-tissue trauma is less. The amount of blood-loss is much less. The overall recovery from surgery is speedier and more pain-free. The impact of locking nails on the surgical management of long-bone fractures cannot be overstated.

The installation of a locking nail, which is a long metal rod and will be interchangeably referred to as a rod or a nail, is accomplished by inserting it, through a small skin incision, into one end of the bone, and advancing it into the bone cavity (medullary cavity) so that the rod is embedded within that cavity. This metal rod has preformed holes at intervals along its length for receiving screws that are inserted transversely or obliquely through the shaft of the bone. In this way the traversing screws lock the bone fragments to the embedded rod, or conversely, lock the rod to the bone. Each traversing screw is inserted into the bone through a small skin incision, and herein lays the problem.

For the placement of each traversing screw, the technical problems for the surgeon include, firstly, making the small skin incision at the correct location and correct angle on the skin surface, and extending the incision through the skin and soft-tissues, down to the bone surface. Instruments are now passed through this small skin and soft-tissue path, to drill a hole that passes through one side of the bone, through the unseen hole in the rod, and into the bone on the far side of the rod.

The challenge of finding the exact spot on the bone's outer surface to drill the first hole, and then to drill in precisely the right direction for the drill bit to pass centrally through the hole in the rod, has been ingeniously solved by the use of a targeting guide. The targeting guide is attached to an outrigger that is rigidly, and removably, attached to one end of the rod. When the nail is embedded in the bone, this attached outrigger and targeting guide protrude from the insertion wound, and lie outside the body. Note that in some device brands, the outrigger and targeting device are a single part. The targeting guide lies parallel with the embedded nail. Within the targeting guide, along its shaft, are tunnels (the targeting guide tunnels) that line up precisely with the holes in the embedded, and unseen, rod. In placing a screw through the bone and the hole in the embedded rod, various instruments are passed through the matching targeting guide tunnel in the targeting guide. Drill bits are long and narrow and sometimes brittle, and their rotating motion can damage soft-tissues. For this reason they are supported and guided, and the tissues are protected from them, by passing them through a metal sheath, the drill-guide. There is no standard nomenclature in the industry for the terms "outrigger", "targeting guide" and "targeting guide tunnel", but the usage of these terms in this patent application can leave no doubt as to the meaning of these terms as used here.

The drill guide is a metal tube that has an outer diameter such that it snugly passes through the matching targeting guide tunnel. The inner diameter of the drill guide is such that the drill bit snugly passes through it. Its leading edge cones down to a bullet-nose.

As a first step for inserting a screw through the wall of the bone and into the underlying rod-hole, the drill-guide is inserted into the matching targeting guide tunnel. The drill guide is advanced to the skin. A mark is made at the site of skin contact. The drill guide is withdrawn, and an incision is made through the skin and soft-tissues until the scalpel blade reaches the bone.

The drill guide is now advanced through this skin incision and soft-tissue path, until its advancing end comes into contact with the bone. The drill-guide, thus placed, is now perfectly located to guide a drill bit to the correct site on the surface of the bone, at precisely the correct angle, to drill through the bone and through the hole in the rod. The drill bit is then advanced deeper into the bone, or out through the opposite cortex (wall) of the bone. Once a hole has been drilled through the bone and the hole in the rod, the drill guide is removed from the targeting guide tunnel and a screw guide sleeve is inserted into the targeting guide tunnel. The screw guide sleeve is used to guide the screw and the screwdriver to the nearside hole in the bone, and through it to the hole in the nail, and out through the hole into the bone on the other side of the nail.

The current practice for cutting the skin incision and a path through the soft-tissues down to the bone is crude and imprecise. The current practice starts wherein the skin entry-site is located by advancing the drill guide through its targeting guide tunnel until it touches the skin. A mark then is made on the skin at the contact site. The drill guide is partly withdrawn away from the skin but is left in the targeting guide tunnel. The surgeon then makes a free-hand skin incision at the marked skin site, using a regular, standard, single-bladed scalpel. The bulky targeting guide blocks direct access to the skin and the surgeon has to work around it. The only direct access to the marked skin site would be though a targeting guide tunnel. As things currently stand, the scalpel is now directed in front of or behind the targeting guide, angled obliquely through the skin incision and soft-tissues, at an approximately anticipated compensating angle, to a mentally calculated and imprecise location on the bone surface. Because this is not the best angle for the incision, the surgeon makes an oversized, irregular skin cut and soft-tissue path that is not at an ideal angle.

For the scalpel to make the skin incision and soft-tissue path at the correct angle and with the shortest path from the skin to the bone would require that the scalpel pass directly though the targeting guide tunnel. Since the targeting guide tunnel guides the drill guide to the precise location on the bone for drilling the hole into the bone, the same tunnel could usefully serve to accurately guide a scalpel through the skin and soft-tissues to the same, precise target point on the bone.

One problem with this solution is that commercially available scalpels do not have handles that are long enough to pass through the targeting guide tunnel and cover the distance down to the bone. If the a scalpel had a longer handle, the surgeon could make a straight pass with the blade, directly through the targeting guide tunnel, through the skin and soft tissues, and down to the bone.

The above solution by itself is not presently viable because an incision made through the targeting guide tunnel with the currently available fixed-blade scalpels would be too small to accommodate the drill guide or the screw driver sleeve. This is because the widest blade that could pass through the targeting guide tunnel would have a width equal to the internal diameter of the targeting guide tunnel. However, a skin incision whose length equals the internal diameter of the targeting guide tunnel would be insufficient to allow passage of a cylindrical instrument (such as the drill guide) that has an external diameter that equals the internal diameter the targeting guide tunnel. If the skin had no elasticity, the length of the smallest skin incision that will allow passage of the drill guide can be calculated; it is equal to half the circumference of the drill guide. The circumference (C) of the cylindrical drill guide is calculated as $\pi$ multiplied by the diameter (D) of the drill guide (C=$\pi$D). Thus, if the diameter of drill guide were 10 mm, the circumference of the drill guide would be 3.14 multiplied by 10 mm, which equals a circumference of 31.4 mm. In non-elastic skin the length ($L_I$) of the smallest skin incision that would accommodate the drill guide would therefore be half the circumference (C) of the drill guide. $L_I$=$\pi$D×0.5. Thus, in non-elastic skin, a skin incision 15.7 mm long is needed for a 10 mm cylindrical drill guide to pass through it: i.e. an incision that is 57% longer than the diameter of the cylindrical drill guide. It can be seen that at present, the widest scalpel blade that could pass through a 10 mm diameter targeting guide tunnel, cannot be 15.7 mm wide, but instead only 10 mm wide, and further, that a 10 mm rigidly guided scalpel blade cannot make an incision that is greater than 10 mm wide, such as the 15.7 mm that is needed in the present example, if the scalpel cuts only in a thrusting mode, with no side to side slicing motion. This percentage is constant: in non-elastic skin, the incision needed for passage of a cylindrical instrument will need to be 57% longer than the diameter of that instrument for all sizes of instrument.

Human skin does have elasticity, and normally, an incision in human skin will stretch 25% to 30%. This is still less than the 57% needed for a cylindrical instrument to pass through a skin incision that equals in length the diameter of that cylindrical instrument.

Therefore, even allowing for the elasticity of normal human skin, the widest, fixed-blade scalpel blade that could be passed through any size targeting guide tunnel could not make a skin incision adequate for the passage of the corresponding drill guide.

Given the elasticity of human skin, the present invention scalpel instruments can make an incision that is less than the 57% enlargement, and still be adequate.

Assuming a skin stretch of 25%, a 12.6 mm incision will stretch to 15.75 mm, which is sufficient for the passage of a 10 mm cylindrical instrument. This is 2.6 mm (26%) greater than the drill guide diameter of 10 mm.

In summary, assuming a skin incision that will stretch 25%, the incision will need to be 26% longer than the diameter of any cylindrical instrument, to enable the said instrument to pass through that incision.

Locking screws placed through the lateral aspect of the proximal femur have to pass through a tough, inelastic fascial layer, called the fascia lata. The fascia lata poses a special problem over the proximal femur in locking nail fracture fixation. The iliotibial band is not quite as thick or tough as the fascia lata, but it poses a similar problem over the lateral aspect of the distal femur. The term "deep fascia" will be used to describe either. The deep fascia forms a barrier to the passage of the drill guide and other instruments. It lies against the bone at the deepest part of the narrow soft tissue incision tunnel. A pointed knife thrust straight into it will only make a small puncture hole. Slicing motion is required to adequately enlarge the puncture hole for passage of the instruments. It is impossible to enlarge the puncture hole without enlarging the soft tissue tunnel as well, thereby causing additional soft tissue damage.

In current practice, the surgeon passes the scalpel anterior or posterior to the targeting guide and through the skin and soft tissues, to blindly slice the deep fascia. Made in this oblique fashion, the fascial incision does not line up perfectly with a straight line between the targeting guide tunnel and the target point on the bone surface. The surgeon therefore makes long sweeping motions with the tip of the knife, making an unnecessarily oversized fascial incision. The fascial incision cannot be repaired later, since it lies in the depth of a narrow soft-tissue tunnel. The fascia lata connects to the iliotibial band. Both play a vital role in normal gait. Excessive damage to the fascia lata or iliotibial Band may later result in impaired gait.

There are many "perforating" arteries just deep to the fascia lata. The larger the fascial incision the more blood vessels will be cut, causing proportionately increased bleeding.

A tunnel-guided-knife as described herein will predictably make the smallest possible skin and soft tissue incision. However, a sharp-pointed blade plunged through the skin straight down to the bone, and then withdrawn back along the identical path, guided in and out by the rigid targeting guide tunnel, will have a terminal configuration that strictly matches the profile of the blade.

Any blade, other than a chisel-shaped blade, will always have a sharp-pointed leading edge, which will cause the terminal end of the tunnel to be triangular. A chisel-blade is impractical since it will not penetrate the skin. A triangular end-tunnel will be of no consequence where the entire tunnel is through soft tissues, such as fat and muscle. However, the deep facia along the lateral thigh is a tough barrier that lies adjacent to the bone.

Any in-and-out blade, other than a chisel, will penetrate the deep fascia with an incision that is always less than the full width of the blade, and likely to be little more than a puncture point. Enlarging the deep fascial incision with a pointed blade would require side-to-side slicing motion, which is not possible with a fixed blade, attached to a rigid cylindrical handle, which is guided by a rigid targeting guide tunnel. Making a minimal incision in the deep fascia at the terminal end of a minimal skin and soft tissue tunnel thus represents a special challenge in using a tunnel-guided knife.

For the sake of speed and convenience, given the technical problems of blindly passing a scalpel anterior or posterior to the targeting guide, surgeons frequently make an initial skin incision, soft-tissue path and fascial incision that is much larger than the minimum needed to get the job done. Alternatively, the surgeon may start with a small, tentative skin incision and enlarge it when he/she finds that it is too small for the drill guide to pass through. This free hand, secondary enlargement will often result in a jagged incision, and the subsequent healed scar will be jagged and cosmetically unsatisfactory.

Additionally, skin incisions and soft-tissue tunnels must be made for each screw, and there is at least one and generally multiple screws that must be applied. At the end of the operation the surgeon has to close each of the individual skin wounds, a process which can be time-consuming, the total time being directly related to the length of each incision.

In the operation of locking nail fracture fixation, there are compelling reasons for the locking-screw incisions through the skin, soft tissues and deep fascia to be as small as possible. The smallest incisions can only be made through the targeting guide tunnel. Ideally each incision needs to be just large enough to accommodate the outer diameter of the drill guide. Skin and soft tissue incisions made through the targeting guide tunnel with a fixed-blade scalpel are too small. A pointed knife thrust straight into the deep fascia through the targeting guide tunnel will only make a small puncture hole, and slicing motion is required for an adequate incision.

SUMMARY OF THE INVENTION

The present invention is a multi-functional double bladed surgical tool. The present invention resolves all the problems discussed above. The present invention is a method and a surgical instrument for predictably and efficiently making the skin incision, soft-tissue path and deep fascial incision, with the smallest, least damaging, and most precise incision. The present invention makes the quickest, cleanest, most precise incision from the skin to the bone than has been seen in the prior art. Additionally, the resulting incision will be much less traumatic than can be made free hand, with a conventional scalpel. It will also enable the surgeon to make the incision quicker and easier, complete the surgery quicker and easier, and allow the patient to heal with less scarring and with less likelihood of, and reduction of adverse secondary effects.

The present invention also relates to a method and apparatus for efficiently making a skin incision and a soft-tissue path from the skin to the bone. The invention herein relates more specifically to a surgical method and a surgical instrument, heretofore unseen in the prior art, for making a skin incision and soft-tissue path from the skin to the bone, and for making the smallest, least damaging, most precise skin incision and soft-tissue path to the bone, and doing so in a manner that is quicker and easier for the surgeon and resulting in the overall operation being quicker and easier for the surgeon, and the patient experiencing less trauma, less scarring, greater healing and less likelihood of damaging or adverse side effects.

Described herein is a method and novel instrument for making an incision of precise and minimal dimensions, in a precise and exact direction, having the shortest path from the skin to the bone. The result is the smallest skin and soft-tissue incision possible, made speedily and accurately. It will be seen that this additionally results in the least amount of tissue trauma possible, shortened operating and anesthesia time, and less blood loss. Further, the incision is easier to repair, and heals with a cosmetically superior scar.

Additionally described herein, is a technique and instrument for making a skin and soft-tissue incision utilizing the targeting guide. Since the targeting guide tunnel guides the drill guide to the precise location on the bone for drilling the hole into the bone, the same targeting guide tunnel can usefully serve as the perfect targeting device for guiding a scalpel through the skin and soft-tissues to the same target point on the bone. In order to do so, the scalpel handle will need to be a cylinder. Conventionally, scalpel handles are flat in order to give the surgeon maximum, ergonomic, manual control over the direction and rotation of the cut. However, a scalpel with a cylindrical handle having a diameter that is the same as that of the targeting guide tunnel through which it is being passed will be provided maximum directional control by the targeting guide tunnel. The surgeon's wet, gloved hand may still have difficulty with rotational control over the smooth cylindrical handle, and therefore the blade. This can be overcome by flattening opposite surfaces of the cylindrical handle so that the handle becomes a partial cylinder. Thus, regardless of the shape of the handle, so long as its perimeter fits snugly within the inner diameter of the targeting guide tunnel, the goals and advantages of the present invention will be achieved.

The present invention further overcomes the problem that presently available conventional scalpels are six to eight inches long, which is insufficient to achieve the objectives of the present invention. The barrel of the present invention scalpel instrument will be longer to pass through the targeting guide down to bone, and still leave sufficient handle protruding for the surgeon to grasp.

The present invention further overcomes the problems with the prior art scalpels by creating a scalpel instrument that is capable of achieving the objectives of the invention. The present invention apparatus is a novel scalpel instrument that can be passed through the targeting guide tunnel to accurately make a most minimal but adequate incision to accommodate the drill guide and other instruments.

In a first embodiment, two or more blades are employed to form the cutting edge. The present invention teaches a means for radially narrowing the cutting edge of the blades of the scalpel instrument for inward passage through the targeting guide tunnel, a means for radially restoring the blades and their cutting edge to its full width after passage through the targeting guide tunnel in preparation for making an adequate skin incision, and a means for radially narrowing the blades and their cutting edge for withdrawal of the scalpel through the targeting guide tunnel after the incision has been made.

The present invention also teaches a means for accurately and predictably making a most minimal but adequate, incision in the deep fascia, at the exact and precise location that it is needed, by means of the two blades functioning together as a surgical scissors apparatus, or viewed alternately as two blades each independently making slicing incisions in the deep fascia. The present invention teaches a means for making the blades of a single instrument function interchangeably as a surgical scalpel and a surgical scissors. The present invention teaches the method of making a cruciate incision in the deep fascia as being the most minimal, least damaging incision possible In a second embodiment, the present invention teaches a means for creating an adequate incision using a single-blade scalpel, wherein the blade rotates for deployment.

The innovative and novel scalpel instruments of the present invention may be made available with barrel handles of different diameters. The surgeon selects a scalpel of suitable barrel diameter to match the targeting guide tunnel of the manufacturer-specific locking nail device in use. For each scalpel barrel diameter, the cutting edges will make adequate skin and fascial incisions to accommodate passage of instruments of matching diameter, through the resulting skin and deep fascial incisions. The present invention scalpel could be used with the instrumentation of any locking nail manufacturer, as long as the correct scalpel barrel diameter is selected to fit that targeting guide tunnel.

The cutting edge of the first embodiment of the present invention scalpel instrument contracts radially for inward passage through the targeting guide tunnel, then expands radially for making the incision, and again contracts radially for the exit passage through the targeting guide tunnel. The mechanism for causing the cutting edge of the scalpel to expand or contract radially is immaterial to the apparatus, method, technique, objectives, and principles described in this patent. It is within the scope of the present invention that the mechanism for causing the cutting edge of the scalpel to expand or contract radially could utilize alternative methods, or use one or more blades to achieve the same desired result.

In the preferred embodiment and method, two or more blades are mounted within the scalpel barrel, near the leading edge of the scalpel. In the contracted position of the blades, the cutting edge does not protrude radially beyond the profile of the scalpel barrel. A mechanism actuated by the surgeon causes the blades to protrude radially from the handle when needed. The blades are configured in such a way that, in the radially protruded position, they act together, as a single cutting edge that is wider than the scalpel barrel. The two blades are also configured so that in moving from the contracted to the protruded position and back again the blades function together as a surgical scissors. A single instrument thus functions interchangeably as a scalpel and a surgical scissors.

The present invention method and scalpel instrument is discussed here for illustrative purposes as used in orthopedic surgery. This description in no way implies that the use of the knife, or the technique, is limited to orthopedic surgery, limited to fracture surgery, limited to surgery on bone, or limited to surgery on humans.

Further novel features and other objects of the present invention will become apparent from the following drawings, detailed description and discussion.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention.

Figure 1:
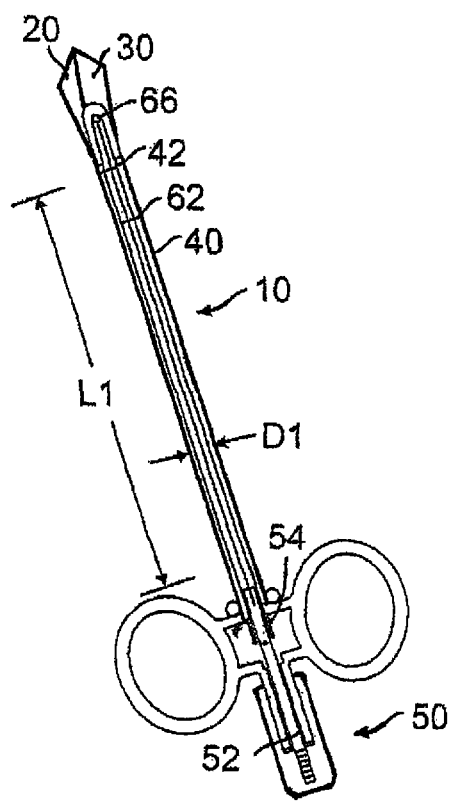
FIG. 1 is a plan view of a preferred embodiment of the present invention scalpel instrument illustrating the position wherein the two blades are radially expanded and in a convex V-shape configuration.
Figure 2:
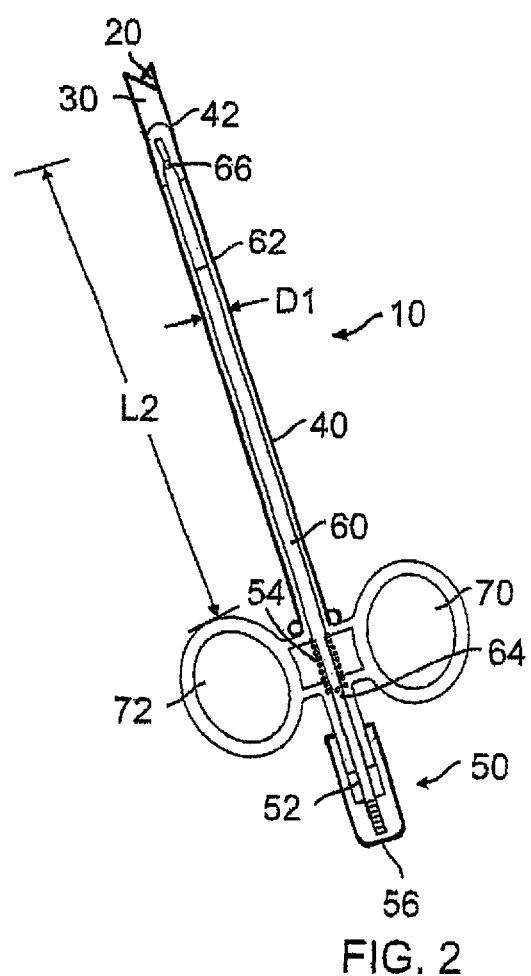
FIG. 2 is a plan view of a preferred embodiment of the present invention scalpel instrument illustrating the position wherein the two blades are radially retracted and in the concave V-shape or open-scissors position.
Figure 5:
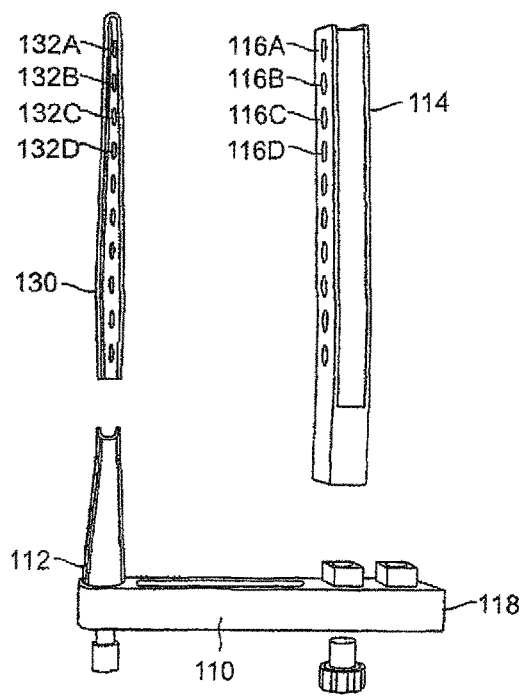
FIG. 5 is an exploded view of the insertion device of the locking nail, including a locking nail, a targeting device, and an outrigger.

In FIGS. 1 and 2, there is shown a preferred embodiment of the present invention scalpel instrument 10. The scalpel instrument 10 preferably has two blades 20 and 30, but may have one or more. The scalpel instrument 10 has a long barrel 40, having a length L1" that is long enough to traverse the length of a targeting guide tunnel and further extend through the skin and soft-tissue of a patient to the patient's bone. It has been found that the preferable length L1" of the barrel 40 is nine and a half inches to meet most current requirements, however the length of the barrel 40 may be whatever length is surgically required. The diameter D1 of the barrel 40 is preferably the same as the inner diameter of the targeting guide tunnel 116A, 116B, 116C, 116D, 116E etc. as illustrated in FIG. 5. As targeting guide tunnels come in different diameters, the scalpel instrument 10 of the present invention may come in corresponding diameters. Additionally, it is preferable that the barrel 40 of the present invention scalpel be shaped as a circular cylinder, but may also be of any shape, such as triangular, rectangular, octagonal, and so on, as long as the outer diameter D1 of the barrel 40 fits snugly within the inner diameter of the targeting guide tunnel.

Figure 3:
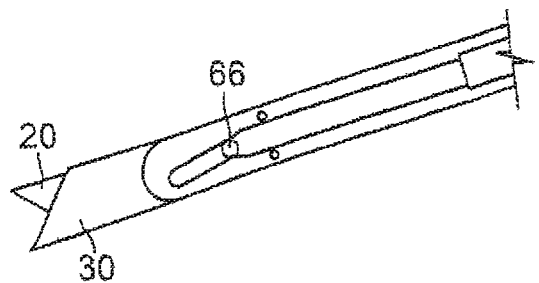
FIG. 3 is a detail of a preferred embodiment of the present invention scalpel instrument with the cutting edges of the two blades in the concave V-shape or open scissors formation, the illustration in a partially open condition to show the actuation mechanism.

The scalpel instrument 10 also has two blades 20, 30. While the scalpel instrument 10 may have any number of blades, the preferred embodiment is shown with two blades 20 and 30. In the default position, the two blades 20 and 30 lay one atop the other with their cutting edges facing the centerline, as best illustrated in FIGS. 3 and 4A.

The blades 20 and 30 are expanded and retracted by a retraction means 50. The retraction means 50 may be of any form, but are here shown as a spring-loaded plunger 52 with a finger hold 70 and 72 located near the proximal end 64 of a plunger rod 60 and may or may not have a transverse rod 66 located at the tip of the distal end 62. The preferred embodiment utilizes a transverse rod 66, but the objectives of the present invention may be fulfilled by other means such as just the distal tip of the plunger rod 60. If the retraction means 50 is of a spring-loaded plunger 52, the spring 54 may be located anywhere on the apparatus as is useful and required to perform the objectives of the present invention. The two blades 20 and 30 have matching slots 22 and 32 respectively that are identical to each other when the blades 20 and 30 are placed flat one over the other facing the same direction, and are also at an angle to the direction of the plunger rod 60, as shown in FIG. 2 and FIG. 3B. When the blades 20 and 30 are installed, the blades 20 and 30 are facing opposite directions, and therefore, the base of the two slots 22 and 32 are aligned, but the angles of the slots 22 and 32 are now going in opposite directions, as shown in FIGS. 3 and 3B. The transverse rod 66 is engaged in the matching slots 22 and 32 of the respective blades 20 and 30. The default position for the spring-loaded plunger 52 is in the retracted concave V-shape position, as shown in FIG. 2 and detailed in FIGS. 3 and 3B. This corresponds to the fully open position of the scissor blades, 20 and 30. Placing two fingers, such as the first finger and second finger of a hand, into the finger holds 70 and 72, the thumb is available to depress the cover 56 of spring-loaded plunger 52. The thumb depresses the cover 56 and thereby depresses the spring-loaded plunger 52, causing the spring 54 to compress and the plunger rod 60 to move forward up the barrel 40 of the shaft towards the distal end 42 of the barrel 40. As the plunger rod 60 moves forward, the transverse rod 66 advances along the matching slots 22 and 32 until it reaches the ends 24 and 34 of the slots 22 and 32. The transverse rod 66 has pushed both blades 20 and 30 simultaneously upward and because of the slots 22 and 32 of each blade 20 and 30 being oriented in opposite directions, the proximal ends of the two blades 20 and 30 angle outwardly and cross over each other as illustrated in FIG. 3C, so that the proximal ends of the blades expand beyond the confines of the handle, while the pointed tips of the distal ends of the blades 20 and 30 move in corresponding opposite directions, and come together as a single, sharp point in a convex V-shape formation cutting surface of the present invention scalpel, as detailed in FIGS. 3A and 4, and shown in FIG. 1. The cutting edges are thus in the shape of a sharp-pointed, two-edged scalpel. A portion of the blades 20 and 30 resides within the barrel 40 of the scalpel instrument 10 at the distal end 42 of the barrel 40.

Figure 3A:
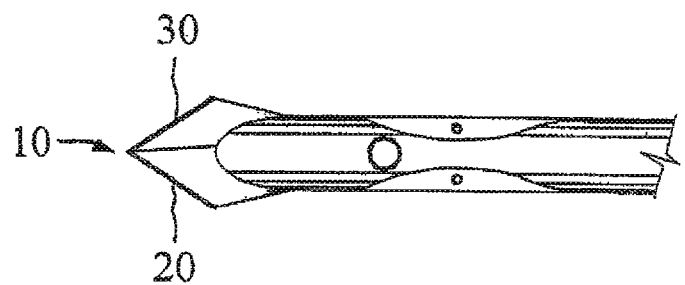
FIG. 3A is a detail of a preferred embodiment of the present invention scalpel instrument with the cutting edges of the two blades illustrated in a convex V-shape radially expanded condition not illustrating the internal actuation mechanism as in FIG. 3
Figure 3B:
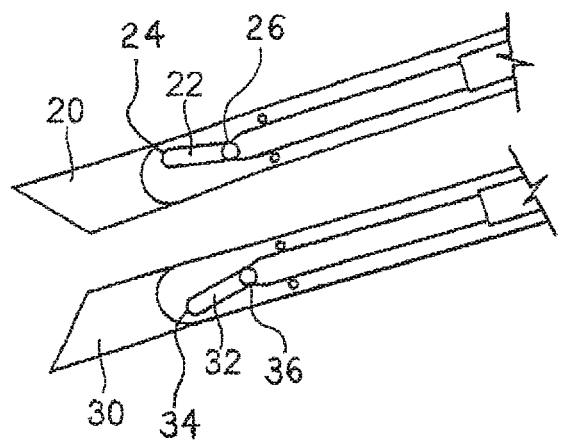
FIG. 3B is a detail of the two blades of the preferred embodiment of the present invention scalpel separated so that the angular slots in each blade are visible.
Figure 3C:
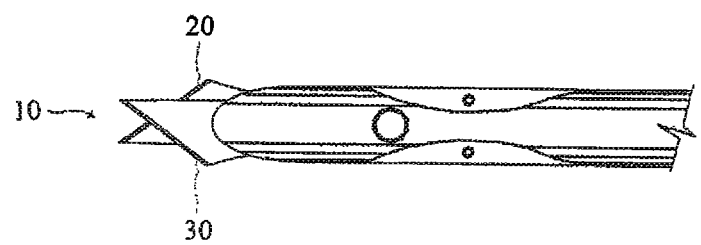
FIG. 3C is a detail of the two blades of the preferred embodiment of the present invention scalpel illustrated with one blade crossing over the other blade during a portion of a scissors-action cycle.
Figure 4:
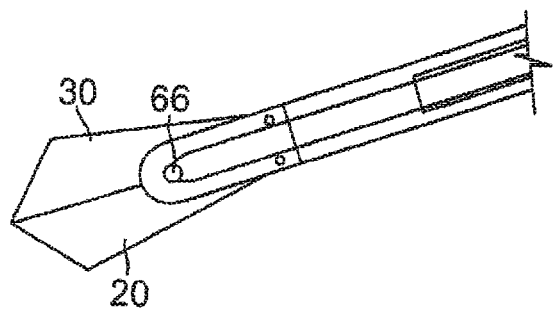
FIG. 4 is a detail of a preferred embodiment of the present invention scalpel instrument illustrating a preferred means of radially expanding the two blades, and the position of the cutting edges of the two blades in the convex V-shape radially expanded, formation, the illustration in a partially open condition to illustrate the actuation mechanism.
Figure 4A:
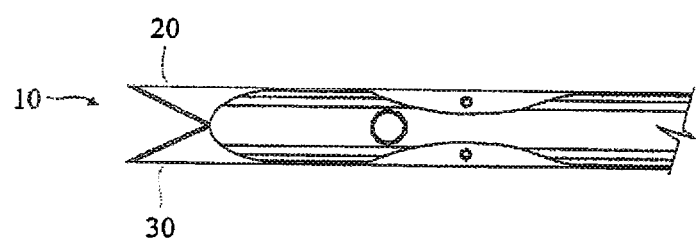
FIG. 4A is a detail of a preferred embodiment of the present invention scalpel instrument illustrating the position of the cutting edges of the two blades in the concave V-shape or open scissors formation, the illustration shown in a totally closed condition and not illustrating the interior actuation mechanism as in FIG. 4.

The fully expanded position of the proximal ends of the blades simultaneously represents the fully closed position of the scissors ends of the blades as seen in FIGS. 3A and 4. The retraction, partial or full, involves the partial or full release of the retraction mechanism, which in the preferred embodiment entails the release of the spring-loaded plunger 52, wherein the plunger rod 60 withdraws down the length L1 of the barrel 40, and the transverse rod 66 will correspondingly withdraw down the matching slots 22 and 32 to engage the aligned ends 26 and 36 of the matching slots 22 and 32 of the blades 20 and 30 causing the blades 20 and 30 to radially retract one over the other and further to withdraw down the barrel 40 of the scalpel instrument 10. It should be noted that when the blades 20 and 30 are in full retraction position, the blades 20 and 30 are in concave V-shape or open-scissors formation, as detailed in FIGS. 3 and 4A. The barrel 40 of the scalpel instrument 10 is long enough to reach the bone in this position.

When the cutting edge of the targeted scalpel forms a sharp pointed convex V-shape, as illustrated in FIGS. 3A and 4, if the scalpel is inserted straight down to the bone through the targeting guide tunnel, and then withdrawn straight out, without any sideways movements, the terminal end of the path made in this manner will be a triangular shaped space that will have the triangular dimensions of the triangular cutting edge, and the deepest part of the path created by the cutting edge will be a point. This will be of little consequence if the present invention scalpel instrument traverses only soft-tissues such as fat and muscle, since the drill guide can easily be advanced to the bone through such soft-tissue, and the objectives of the present invention will be achieved. However, the fascia lata and the iliotibial band lie against the bone and therefore, as soon as the advancing tip of the blade penetrates the deep fascia it will come up against the bone, and will be prevented from further advancement, and from making an adequate incision in the deep fascia, having made only a small puncture hole.

Figure 14:
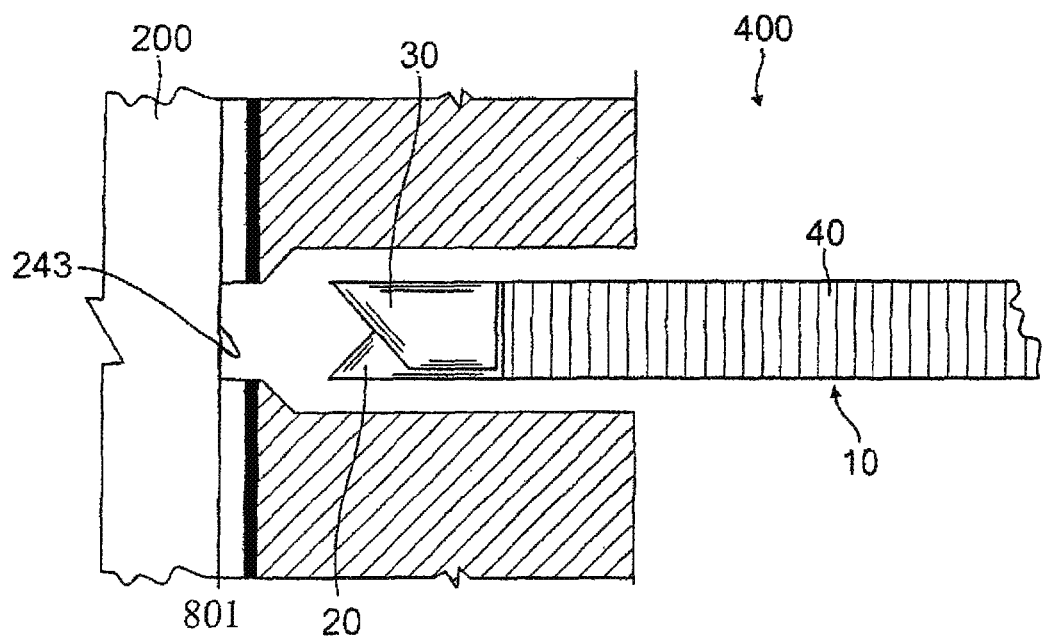
FIG. 14 is a detail illustration, not to scale, of the next step after FIG. 13, of the preferred embodiment of the present invention scalpel instrument in use in the method of the present invention, wherein the blades of the scalpel instrument are in the concave V-shape open-scissors formation, and the scalpel instrument is being withdrawn; the first arm of the cruciate incision has been made by a scissoring action of the present invention scalpel invention, the incision in the deep fascia is narrower than the width of the skin and soft-tissue tunnel.
Figure 14B:
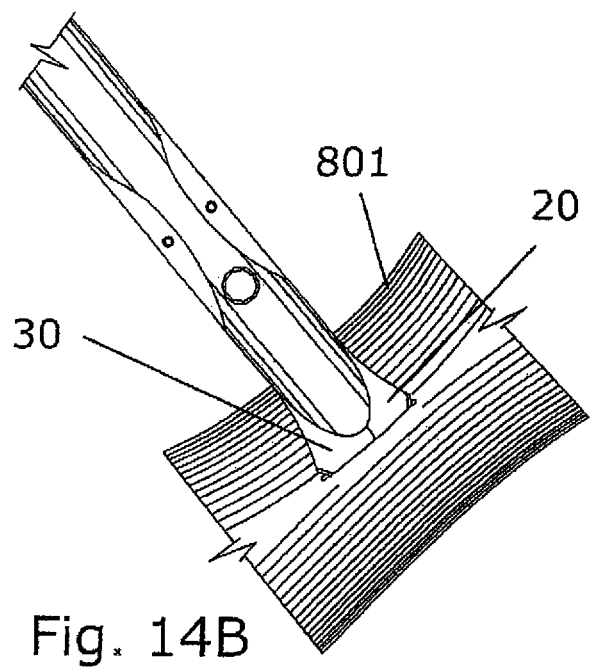
FIG. 14B is a detail illustration, not to scale, of the incision in the deep fascia after the present invention scalpel instrument has punctured the deep fascia in the concave V-shape position with the two blades having moved toward each other in a scissors-action and have completed the first arm of the cruciate incision in the deep fascia.
Figure 14A:
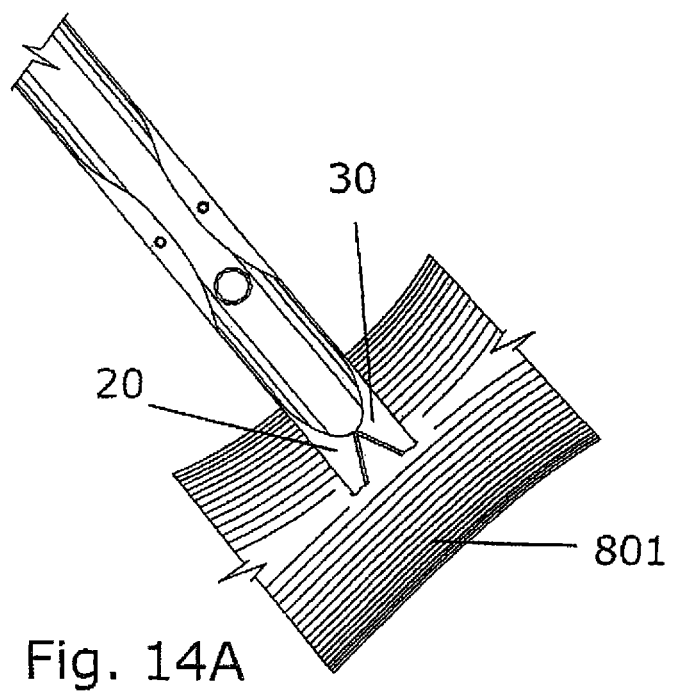
FIG. 14A is a detail illustration, not to scale, of the first step in making a cruciate incision in the deep fascia, the two blades of the present invention scalpel instrument have punctured the deep fascia in the concave V-shape position.
Figure 14D:
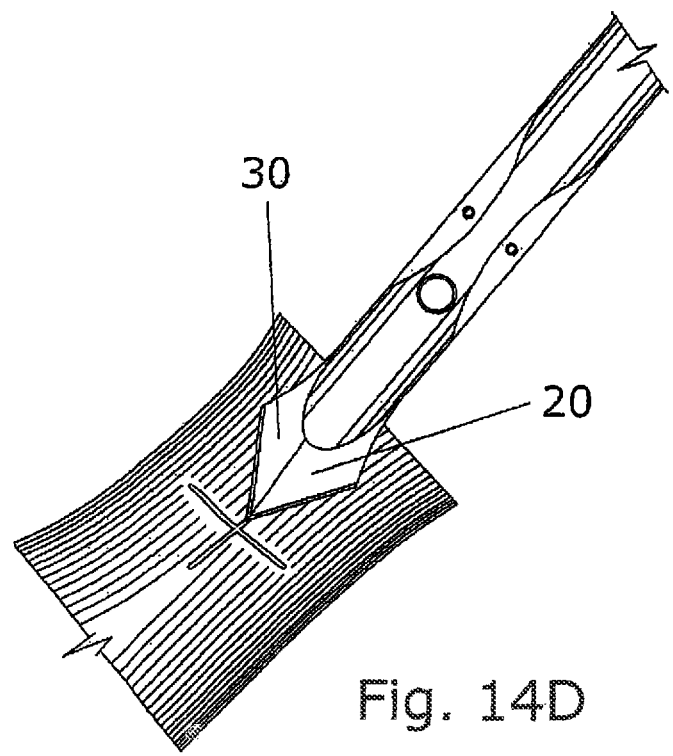
FIG. 14D is a detail illustration, not to scale, of the next step in the method, illustrating the preferred embodiment of the present invention scalpel instrument being withdrawn from the cruciate incision, after completing the second arm of the cruciate incision by a scissors action, thus making a cruciate incision in the deep fascia with two equal arms, an incision large enough to allow passage of the bullet-nosed leading end of the drill guide to pass through the deep fascia and down to the surface of the bone as seen in FIGS. 14E and 14F, thereby allowing full access to the bone and the future placement of a screw unimpeded and without further damage to the soft-tissue, through the most minimal incision that could be made to accommodate the bullet nose of the drill guide.
Figure 14C:
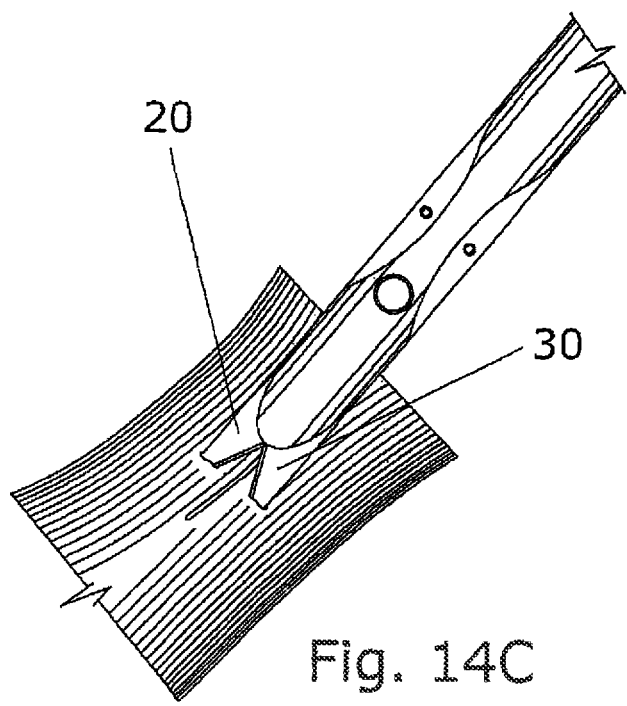
FIG. 14C is a detail illustration, not to scale, of completing the cruciate incision in the deep fascia after the present invention scalpel instrument has punctured the deep fascia in the concave V-shape position and by scissors-action having completed one arm of the cruciate incision in the deep fascia, the scalpel instrument then partly withdrawn and rotated 90 degrees and then advanced toward the bone to penetrate the deep fascia a second time in the concave V-shape position.
Figure 14F:
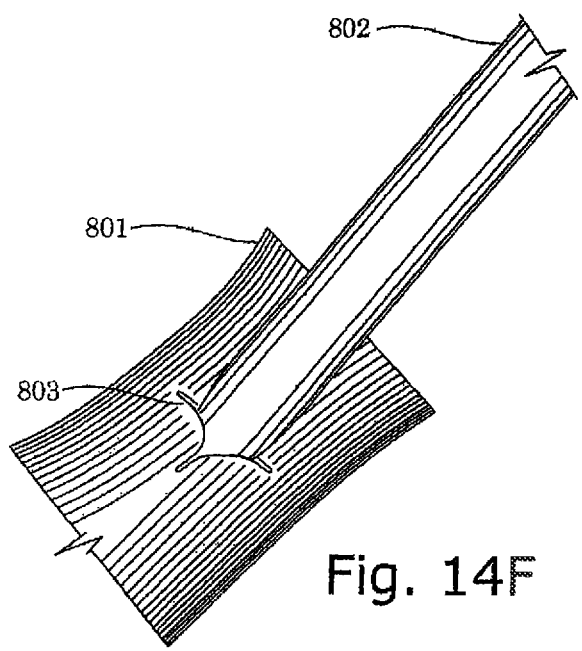
FIG. 14F is the next step in the method, illustrating the bullet-nosed drill guide having passed through the cruciate incision in the deep fascia and against the bone, in readiness for the drill to pass through the drill guide and drill a hole through the bone for placement of a screw into the bone.
Figure 14E:
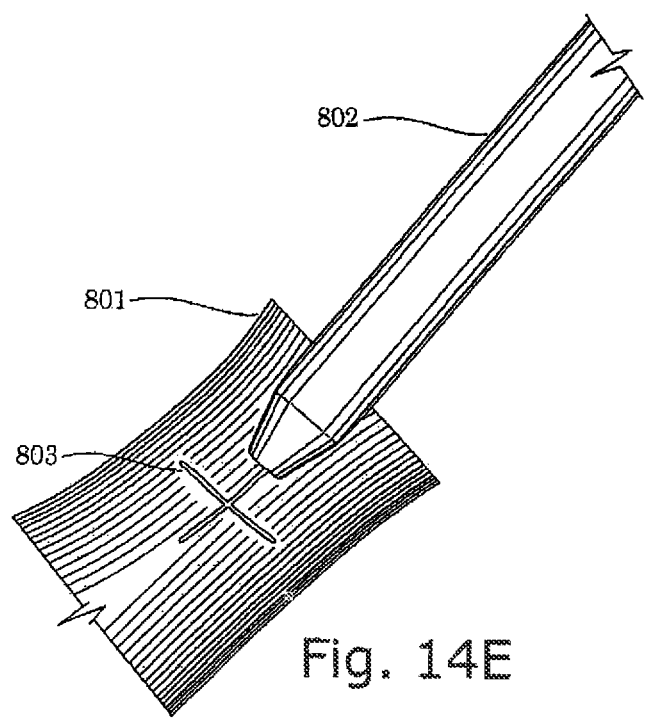
FIG. 14E is a detail illustration not to scale, illustrating the bullet-nosed drill guide having passed through the targeting guide tunnel, having passed through the soft tissue tunnel in the skin and soft tissues and about to pass through the cruciate incision in the deep fascia.

Although the drill guide has a conical leading end, FIG. 14E, it will not pass through a small puncture hole. The surgeon may safely, easily and quickly overcome the thick deep fascia in the most precise and efficient manner by placing the mobile, two-bladed present invention scalpel instrument in a second cutting position, FIG. 4A. The present invention scalpel instrument may have two blade positions, such that in the first blade position it is configured in a convex V-shape, sharp pointed, double-edged cutting surface with a single point as the leading edge, as shown in FIG. 3A and FIG. 4. A second blade position has two advancing points, which together form the shape of a concave V-shape, as illustrated in FIG. 3 and FIG. 4A. Additionally, the cutting edges of the blades face toward the centerline when they are in the concave V-shape position. In moving from the concave V-shape to the convex V-shape position, the blades cross over each other so that the cutting edges face away from the centerline in the convex V-shape position. As the blades move from the concave V-shape to the convex V-shape position and back again, activated by the surgeon through the spring-loaded plunger, they function as a surgical scissors as seen in FIGS. 4A, 3C and 4.

The surgeon will advance the blade the full distance from the skin to the bone in the first blade position as a convex V-shape until the present invention scalpel instrument's sharp tip touches bone. The present invention scalpel instrument is then withdrawn about one half inch, then is changed to the second blade position, the concave V-shape position, or open-scissors position, and again advanced towards the bone until the two sharp points of the concave V-shape penetrate the deep fascia. The surgeon then depresses the spring-loaded plunger causing the two center-facing cutting edges to move towards each other as surgical scissors, or as two independent slicing instruments, which now complete an incision between the two puncture points. Even then, as discussed before, this single incision will not be wide enough to allow passage of the cylindrical drill guide, because the single incision will only be as wide as the external diameter of the drill guide and in non-elastic tissue the incision needs to be 57% larger than the diameter of the drill guide. Therefore the present invention scalpel instrument, still in the second blade position, concave V-shape configuration, is again withdrawn about one half inch, rotated ninety degrees and again advanced to the bone until the two sharp points again penetrate the deep fascia. Using the scissors-function, a second fascial incision is made at 90 degrees to the first incision, thus creating a cruciate incision. The two arms of the cruciate incision are each only as long as the external diameter of the drill guide, but in the cruciate configuration, the two together create a larger opening in the fascia. In the inelastic fascia such a cruciate incision will still not allow passage of the full drill guide. Fortunately the drill guide has a conical nose, which will easily pass through this smaller cruciate fascial incision.

The present invention method and the present invention scalpel apparatus now have made it fairly easy to advance the bullet-nosed drill guide through this minimal cruciate opening in the deep fascia as seen in FIGS. 14E and 14F. The cruciate incision in the deep fascia, with each of its two arms equal in length to the diameter of the drill guide is therefore the smallest incision possible to accommodate the instruments.

The scalpel instrument described here is unique in that it is two instruments in one: a surgical scissors and a double-edged, sharp pointed surgical scalpel. In the fully retracted position as seen in FIG. 4A, the blades are an open-scissors with the sharp blade-edges facing the centerline. Moving from the retracted position FIG. 4A to the deployed position, FIG. 3A the sharp edges of the two blades move toward each other in a scissoring action. The blades cross over each other, FIG. 3C, so that in the fully deployed blade position, FIG. 3A, the two cutting edges face away from the centerline, forming a sharp pointed scalpel, with sharp, side-cutting edges, functioning usefully to puncture the skin, and make an incision as wide as the deployed cutting surface. As the blades move from the contracted to the deployed position and back again with the cutting surfaces facing each other, they usefully function as a surgical scissors. The deep fascia is first pierced by a forward thrusting motion of the two sharp pointed blades in the concave V-shape position or open-scissors position, seen in FIG. 4A, and the first "arm" of the cruciate incision is then completed by the scissoring action of the blades by the two cutting edges moving towards each other. The present invention scalpel instrument is partially withdrawn, rotated 90 degrees, again advanced toward the bone, the two sharp points again penetrate the deep fascia, and the second "arm" is completed by a scissoring action, thus completing the cruciate cut.

The advantages of the present invention method and apparatus are numerous. By making an incision through the skin and soft-tissues with the present invention method and scalpel instrument, the surgeon makes a minimal incision quickly and accurately. The skin incision and soft-tissue path will be precisely the correct width needed for passage of the drill guide and other instruments, the incision through the deep fascia will be slightly smaller but adequate for the passage of the bullet-nosed drill guide, damage to the fascia lata, iliotibial band and other soft-tissues will be minimized, bleeding will be decreased, the time to make the incision will be shorter, the time taken to close each wound will be shorter, the time under anesthesia will be shortened, and the resulting scar will be more cosmetic.

The surgical scalpel of the present invention is tunnel guided through human or animal skin and soft tissues to its destination at the surface of any underlying bone. This requires an adequate cutting surface that is thrust forward along the path of the knife. It is preferable for the soft-tissue tunnel to have the same width all along its length, from the skin incision to the bone. The present invention scalpel in the convex V-shape configuration creates such a tunnel from the skin to the fascia. However, the sharp-pointed blade only makes a puncture hole in the deep fascia. Then, by a scissor cutting method, a cruciate incision is made in the deep fascia that is smaller than the soft tissue tunnel, but sufficient for passage of the bullet nose of the drill guide.

It is a well-known fact that the slightest contact of a scalpel's cutting edge against any metal surface will immediately dull the sharpness of the cutting edge. If a scalpel is used that has an advancing edge in a convex V-shape configuration, that is with its blades facing away from the center line of the blade, in passing the tunnel guided knife through a metal tunnel guide there is great likelihood that some or all of the cutting surfaces will touch the sides of the metal targeting tunnel guide at least some point along its excursion, especially as the knife edge is being introduced into the opening of the targeting guide tunnel. The sharp cutting edges of a knife in the concave V-shape, where only the inner edges of the concave V-shape are sharp and the outer edges are dull will therefore be protected from any such metal-to-metal contact.

Additionally, since the sharp cutting edges of each of the multi-blade embodiments of the present invention face inwards, and the dull outer edges outward, there is less likelihood that operating room personnel will cut themselves on the blades. Additionally, since all the cutting surfaces face inwardly in the concave V-shape position, the cutting surfaces described here will only cut on forward thrusting, or on scissoring. Therefore the skin cannot be additionally, accidentally, cut on withdrawal of the instrument, even if this instrument is unintendedly rotated upon withdrawal.

Figure 6:
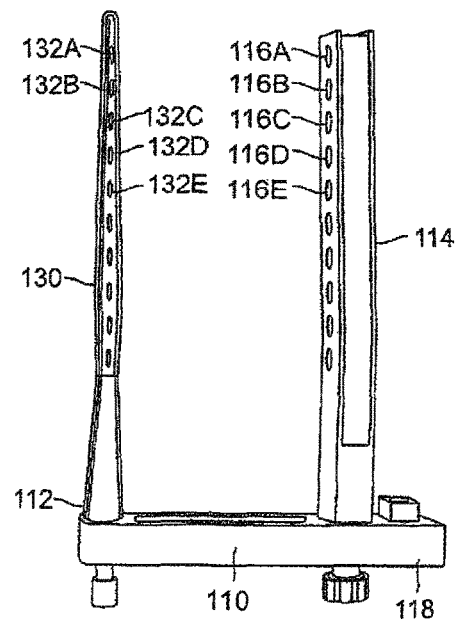
FIG. 6 is a perspective view of a locking nail, a targeting device and an outrigger, joined together, illustrating the relationship of the three to each other.
Figure 7:
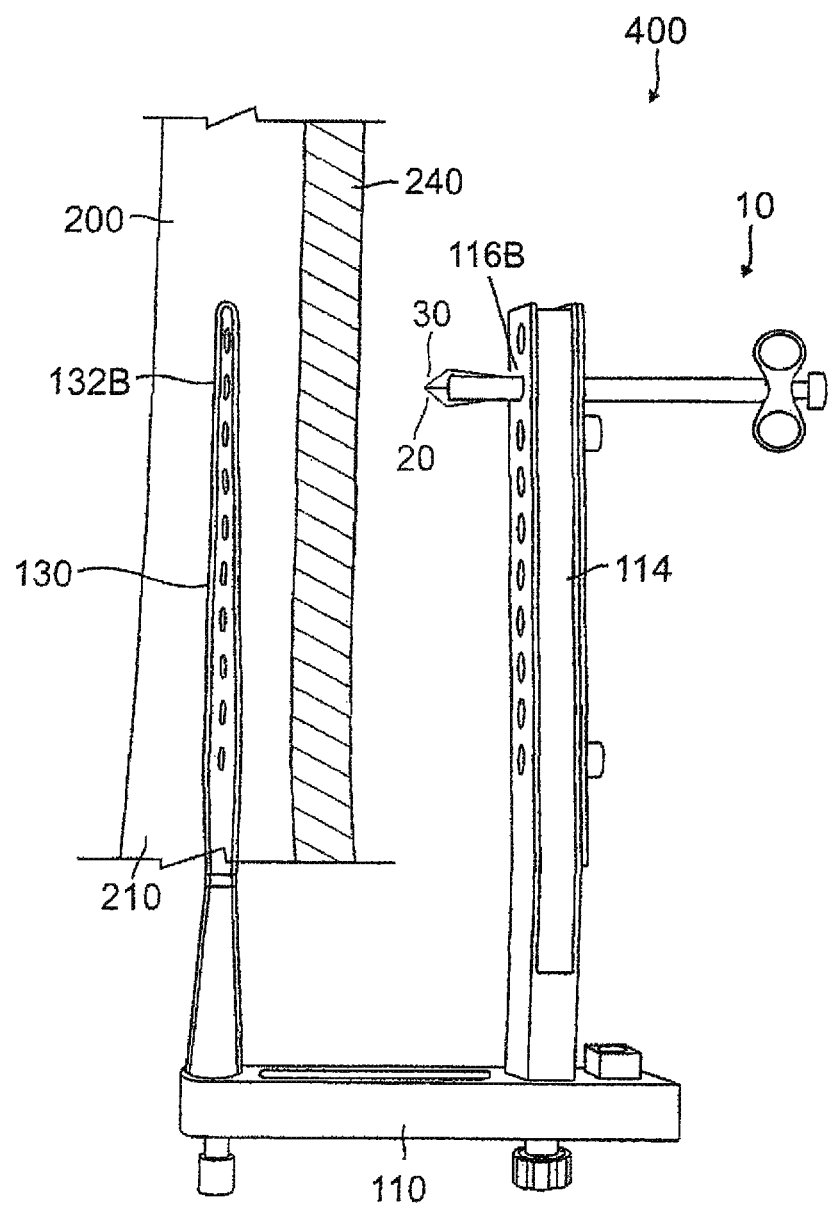
FIG. 7 is an illustration, not to scale, of a partial cross-section of a bone covered with skin and soft tissues with the locking nail inserted into the bone and a perspective view of the aligned targeting guide in place with the present invention scalpel instrument inserted through a targeting guide and the deployed blades moved out of the scalpel and presented to and about to penetrate the skin and soft tissues with the scalpel blades in a convex V-shape formation.

Referring now to the FIGS. 5 through 17, there is shown the method 400 and apparatus 10 for making a precise and minimal skin and soft-tissue tunnel, and a minimal cruciate incision in the deep fascia. In FIGS. 5, 6 and 7 there is shown an outrigger 110 to which a locking nail 130 is attached at a first end 112 of the outrigger 110 and a targeting device 114 is attached at a second end 118 of the outrigger 110. A locking nail 130 is inserted into the bone 200, usually through the base 210 of the bone 200. The locking nail 130 has multiple screw holes 132A, 132B, 132C, 132D, 132E, etc. through which a screw 140, see FIG. 16, will be affixed, however once the locking nail 130 is inserted into the bone 200, the screw holes 132A, 132B, 132C, 132D, 132E cannot be seen. The targeting guide 114 has numerous holes, the targeting guide tunnels, 116A, 116B, 116C, 116D 116E, etc. that align with the screw holes 132A, 132B, 132C, 132D, 132E, etc of the locking nail 130. The locking nail 130 and the targeting guide 114 are each removably affixed to the outrigger 110, which, among other things, maintains the alignment of the screw holes 132A, 132B, 132C, 132D, 132E, etc. of the locking nail 130 and the corresponding targeting guide tunnels 116A. 116B, 116C, 116D, 116E, etc. of the targeting guide 114. Once it has been determined which screw hole 132A, 132B, 132C, 132D, 132E of the locking nail 130 should be engaged with a screw 140, a targeting guide tunnel 116 is selected from hole 116A, 116B, 116C, 116D, 116E, etc. which corresponds to a respective hole 132A, 132B, 132C, 132D and 132E in the locking nail 130. For purposes of illustration only, the targeting guide tunnel 116B is now in position exactly where the screw hole 132B of the locking nail 130 is located at the exact angle at which the screw 140 will be inserted and affixed to the locking nail 114, and is now in position for the present invention scalpel 10 to create a soft-tissue tunnel 230, followed by insertion of the screw 140, and surgical closing procedures.

FIG. 7 is a partial cross-section of a bone 200 covered with skin and soft tissue 240 with the locking nail 130 inserted into the bone 200 and a perspective view of the aligned targeting guide 114 in place with the present invention scalpel instrument 10 inserted through a targeting guide tunnel 116B in the targeting guide 114 and the blades 20 and 30 moved out of the scalpel 10 and about to enter the skin 240 with a convex V-shape point for the scalpel blades 20 and 30.

Figure 8:
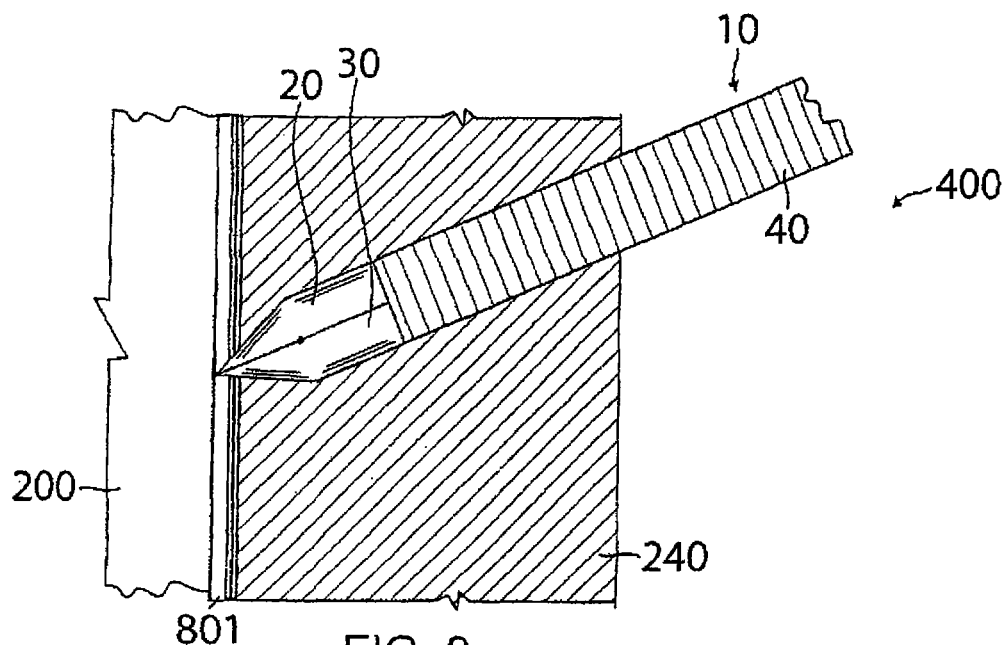
FIG. 8 is a detail illustration of prior art and the presentation of prior art scalpel advanced through the skin and soft-tissue to a bone.
Figure 9:
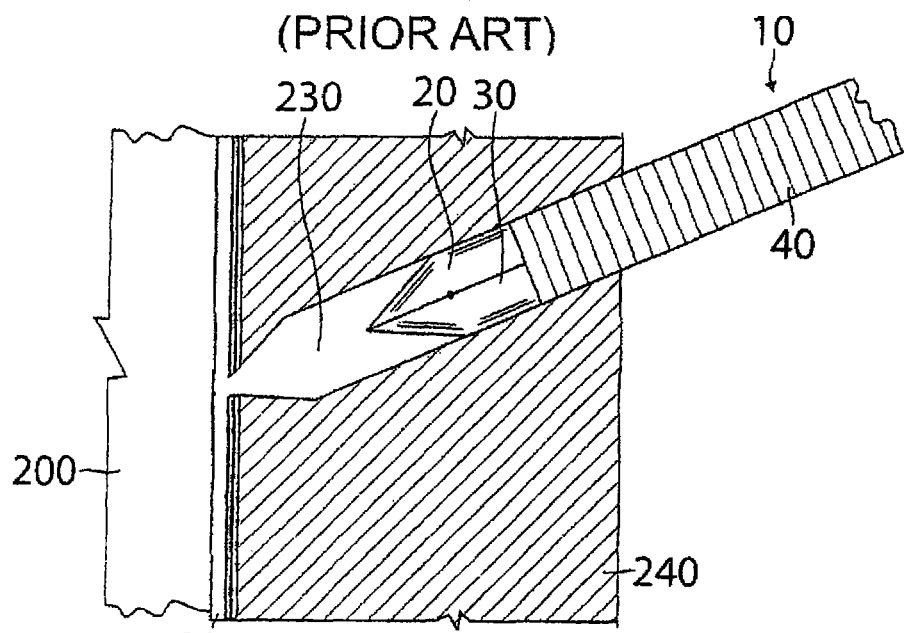
FIG. 9 is a detail illustration of prior art and the inadequacies of the incision and soft-tissue tunnel to the bone.

FIGS. 8 and 9 are examples of prior art and limitations thereof when making an incision and soft-tissue tunnel. It can be seen that current methods of creating an incision and a soft-tissue tunnel, are performed crudely and unguidedly. The surgeon must present the scalpel to the skin at an angle because the scalpel cannot be brought perpendicular to the spot because the targeting device 114, previously shown, is in the way. The surgeon must work around the targeting device 114, which therefore means that the scalpel is presented at an angle that is not 90 degrees to the bone. It can be seen that an incision from this angle through the skin and soft-tissue to the bone, creates an initial incision that is not where a screw 140 will be presented for entrance and is not of the required size. Nor does it create a soft-tissue tunnel that follows the same path that the screw 140 will travel to the bone. Additionally, it can further be seen that the soft-tissue tunnel ends in a single point at the bone. Under current practice, in order to create a skin incision that is located where the screw 140 will be presented, the surgeon must wiggle the scalpel back and forth, in a free-hand manner, to create the initial incision. Additionally, the surgeon must continue to wiggle the scalpel back and forth as it passes through the soft-tissue, so as to create a soft-tissue tunnel that will allow the screw 140 to progress perpendicularly to the fascia, and further, once the scalpel has reached the fascia, the surgeon continues to wiggle the scalpel back and forth, slicing the fascia and scraping against the bone, so as to cut a an oversized, straight line path between the targeting guide tunnel and the point of screw insertion on the bone surface. All of this is performed free hand, without guidance, and with the surgeon guessing the approximate locations of where the scalpel blade is as compared to the tunnel that must be made. It can be seen that quite a bit of skin and soft-tissue is cut, far more than is necessary, to make an incision and soft-tissue tunnel for a screw 140. Usually the surgeon makes a long, longitudinal incision in the deep fascia. If a cruciate incision is made the damage is doubled, as the surgeon performs the above procedure, partly withdraws the scalpel and performs the same procedure blind, entering the previous incision at an angle approximately ninety degrees to the first incision. It can be seen that the prior art is imprecise and creates a greater amount of damage to the patient than what is surgically necessary.

Figure 10:
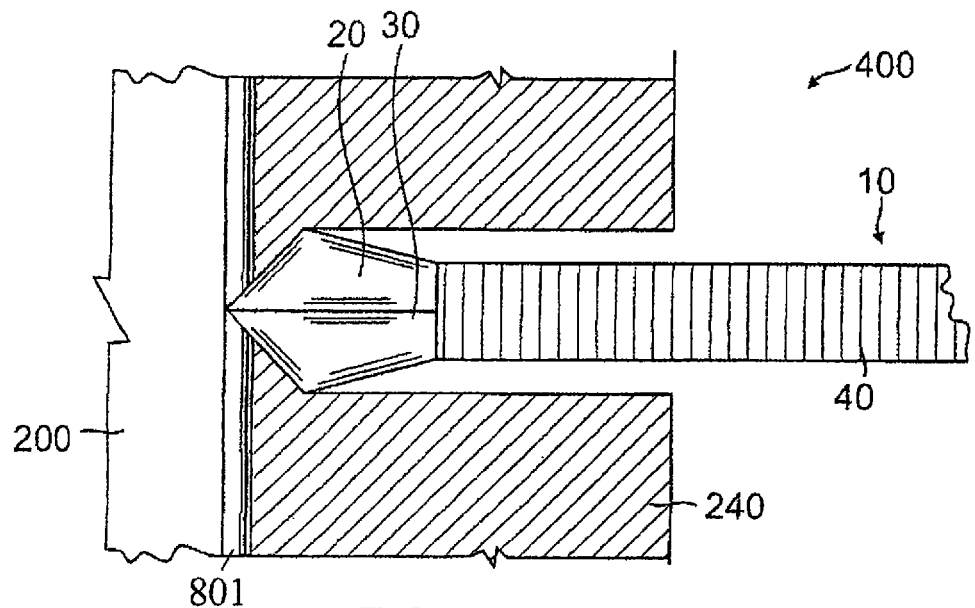
FIG. 10 is a detail illustration, not to scale, the next step after FIG. 7, wherein there is illustrated a cross-sectional view of the preferred embodiment of the present invention scalpel instrument in use in the method of the present invention, wherein the blades of the scalpel instrument are in the convex V-shape formation and have advanced through the skin and soft-tissue, penetrated the deep fascia, and have reached the bone.

FIG. 10 is an illustration of the next step after FIG. 7 wherein there is illustrated a cross-sectional view of the preferred embodiment of the present invention scalpel instrument 10 in use in the continuing method 400 of the present invention, wherein the blades 20 and 30 of the scalpel instrument 10 are in the convex V-shape formation and have advanced through the skin and soft-tissue 240 and reached the bone 200. It can be seen that the skin incision and the soft-tissue tunnel 230 that is created by the present invention is wider than the handle barrel 40 of the scalpel instrument 10, and is at an angle that is the exact path that the screw 140 will follow. It can be seen that the sharp convex V-shape tip of the cutting surface made by the two blades 20 and 30 has penetrated the deep fascia 801, has come to rest against the bone 200, through a small puncture hole, and is prevented from further penetration through the deep fascia 801, by the bone 200, leaving an insufficient pathway through the deep fascia 801 for the bullet-nosed end of the drill guide 802, to pass through.

Figure 11:
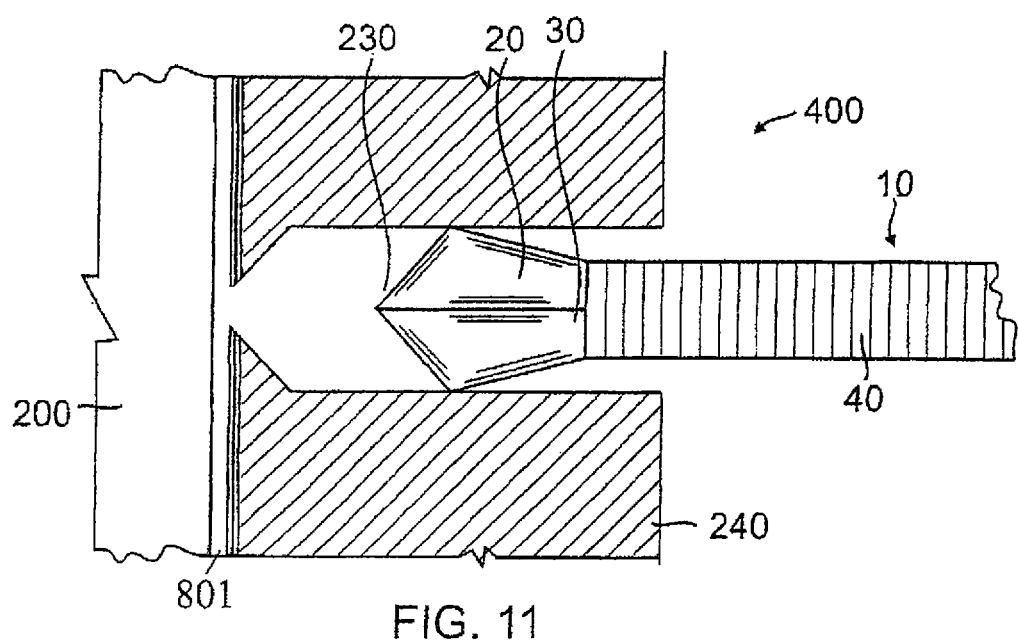
FIG. 11 is a detail illustration, not to scale, of the next step after FIG. 10 wherein there is illustrated a cross-sectional view of the preferred embodiment of the present invention scalpel instrument in use in the method of the present invention, wherein the blades of the scalpel instrument are in the convex V-shape formation, and having reached the bone in FIG. 10, and are now being withdrawn; Also illustrating that a soft-tissue tunnel has been made in the skin and soft tissues from the previous steps; the terminal end of the tunnel is convex V-shaped, the deep fascia has been penetrated by the sharp tip of the scalpel.

FIG. 11 is an illustration of the next step after FIG. 10 wherein there is illustrated a cross-sectional view of the preferred embodiment of the present invention scalpel instrument 10 in use in the continuing method 400 of the present invention, wherein the blades 20 and 30 of the scalpel instrument 10 are in the convex V-shape formation, have reached the bone 200, and are now being withdrawn. It can be seen that at this point the soft-tissue tunnel 230 ends in a convex V-shape formation, matching the shape of the blades 20 and 30 of the scalpel 10, leaving an insufficient opening in the deep fascia 801, for passage of the bullet-nosed tip of the drill guide 802, to pass through. It is desirous that the soft-tissue tunnel 230 does not end with a point at the bone 200. It will be seen that the next steps in the present invention method 400 will create a complete tunnel 230 that will have access to the bone 200, and terminates in the cruciate incision in the deep fascia, and not merely the single point where the two blades 20 and 30 meet the bone 200, as created in this step of the method 400 so far.

Figure 12:
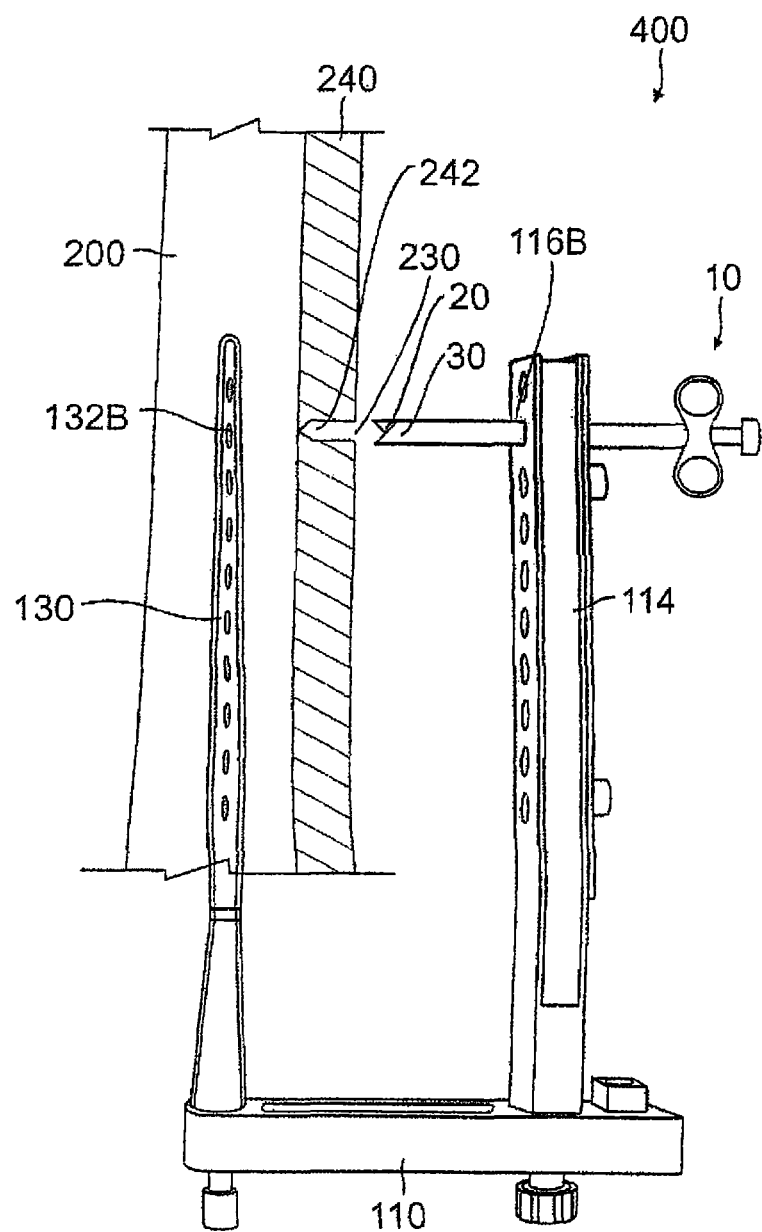
FIG. 12 is an illustration, not to scale, of the next step after FIG. 11 wherein there is illustrated a partial cross-section of a bone covered with skin and soft tissues with the locking nail inserted into the bone and a perspective view of the aligned targeting guide in place with the present invention scalpel instrument inserted through a targeting guide tunnel and the blades in the retracted concave V-shape open-scissors position, also illustrating that a convex V-shape soft-tissue tunnel has been made from the previous steps.

FIG. 12 is a partial cross-section of a bone 200 covered with skin and soft-tissue 240 with the locking nail 130 inserted into the bone 200 and a perspective view of the aligned targeting guide 114 in place with the present invention scalpel instrument 10 inserted through a targeting guide tunnel and the blades 20 and 30 moved into the concave V-shape or open-scissors configuration; also illustrating that the soft-tissue tunnel 230 is, at this step in the method 400, a convex V-shape incision 242 that has been made in the skin and soft tissues 240, and deep fascia 801, from the previous steps.

Figure 13:
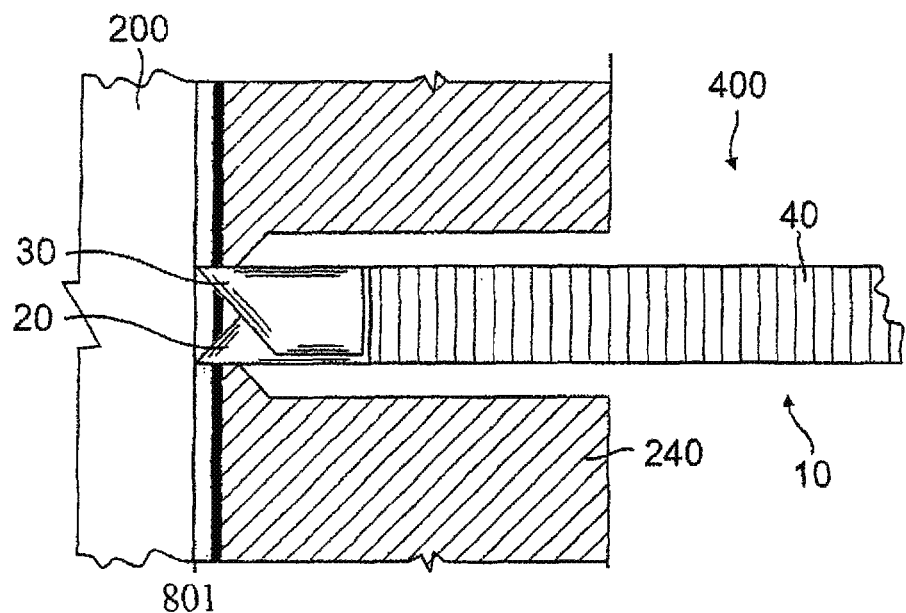
FIG. 13 is an illustration of the preferred embodiment of the present invention scalpel instrument in use in the method of the present invention, wherein the blades of the scalpel instrument are in the concave V-shape open-scissors formation, and the scalpel instrument has traversed the wider soft-tissue tunnel path created by the present invention scalpel when it was in the convex V-shape formation, and has now reached the bone; the two sharp tips of the blades have penetrated the deep fascia and have come to rest against the bone; the incision in the deep fascia has a length equal to the diameter of the drill guide, and not the width of the deployed scalpel blades, and is smaller than the skin and soft-tissue tunnel.

FIG. 13 is a detail illustration of the next step in the method 400 after FIG. 12, wherein there is illustrated a cross-sectional view of the preferred embodiment of the present invention scalpel instrument 10 in use in the method 400 of the present invention wherein the blades 20 and 30 of the scalpel instrument 10 are in the concave V-shape or scissors formation and have traversed the path of the previously made soft-tissue tunnel 230, the sharp tips of the blades 20 and 30 have penetrated the deep fascia 801, reached the bone 200 and, using the scissors action of the blades 20 and 30, are about to make a first incision in the deep fascia 801.

FIG. 14 is an illustration of the next step in the method 400 after FIG. 13, wherein there is illustrated a cross-sectional view of the preferred embodiment of the present invention scalpel instrument 10 in use in the method 400 of the present invention, wherein the scalpel instrument 10 is in the concave V-shape or open-scissors formation, had previously reached the bone 200; had previously made a scissoring incision in the deep fascia 801, and is now being withdrawn. It can now be seen that the soft-tissue tunnel 230 does not end in a convex V-shape incision 242, which was created previously, but now ends in a straight-line incision 243, the scalpel instrument 10 was then partly withdrawn and rotated 90 degrees and advanced toward the bone 200, so that the sharp tips of the blades 20 and 30 of the present invention scalpel 10 have again penetrated the deep fascia creating a second incision in the deep fascia intersecting the first incision at 90 degrees thus creating a cruciate incision 803, through the deep fascia 801, which is slightly smaller than the soft tissue tunnel 230 but which will sufficiently allow passage of the bullet-nosed end of the drill guide 803, to the surface of the bone 200 as seen in FIG. 14E an 14F, thereby allowing full access to the bone 200, and the future placement of a screw 140, unimpeded and without further damage to the soft tissue 240.

FIG. 14A is a detail illustration of the first step in making a cruciate incision in the deep fascia; the two blades of present invention scalpel instrument have punctured the deep fascia in the concave V-shape position.

FIG. 14B is a detail illustration of the incision in the deep fascia after the present invention scalpel instrument has punctured the deep fascia in the "M" position and the two blades have moved toward each other in a scissors-action and have completed the first arm of the cruciate incision in the deep fascia.

FIG. 14C is a detail illustration of the cruciate incision in the deep fascia after the present invention scalpel instrument has punctured the deep fascia in the concave V-shape position and by scissors-action has completed one arm of the cruciate incision in the deep fascia; the scalpel instrument was then partly withdrawn and rotated 90 degrees and then advanced toward the bone to penetrate the deep fascia a second time in the concave V-shape position.

FIG. 14D is a detail illustration of the next step in the method 400, illustrating the preferred embodiment of the present invention scalpel instrument being withdrawn from the cruciate incision 803, after completing the second arm of the cruciate incision by a scissors action. thus making a small cruciate incision in the deep fascia with two equal arms, the length of each arm equal to the diameter of the barrel of the scalpel device, the cruciate incision smaller than the soft tissue tunnel 242, but large enough to allow passage of the bullet-nosed leading end of the drill guide 802 to pass through the deep fascia and down to the surface of the bone as seen in FIGS. 14E and 14F, thereby allowing full access to the bone 200 and the future placement of a screw 140 unimpeded and without further damage to the soft-tissue 240.

FIG. 14E is the next step in the method 400, illustrating the bullet-nosed drill guide 802 having passed through the targeting guide tunnel 116B, having passed through the soft tissue tunnel in the skin and soft tissues 230, and is about to pass through the cruciate incision 803, in the deep fascia.

FIG. 14F is the next step in the method 400, illustrating the bullet-nosed drill guide 802 has passed through the cruciate incision 803, in the deep fascia and is against the bone 200, in readiness for the drill to pass through the drill guide 802, and drill a hole through the bone 200 for placement of a screw 140, into the bone 200.

Figure 15:
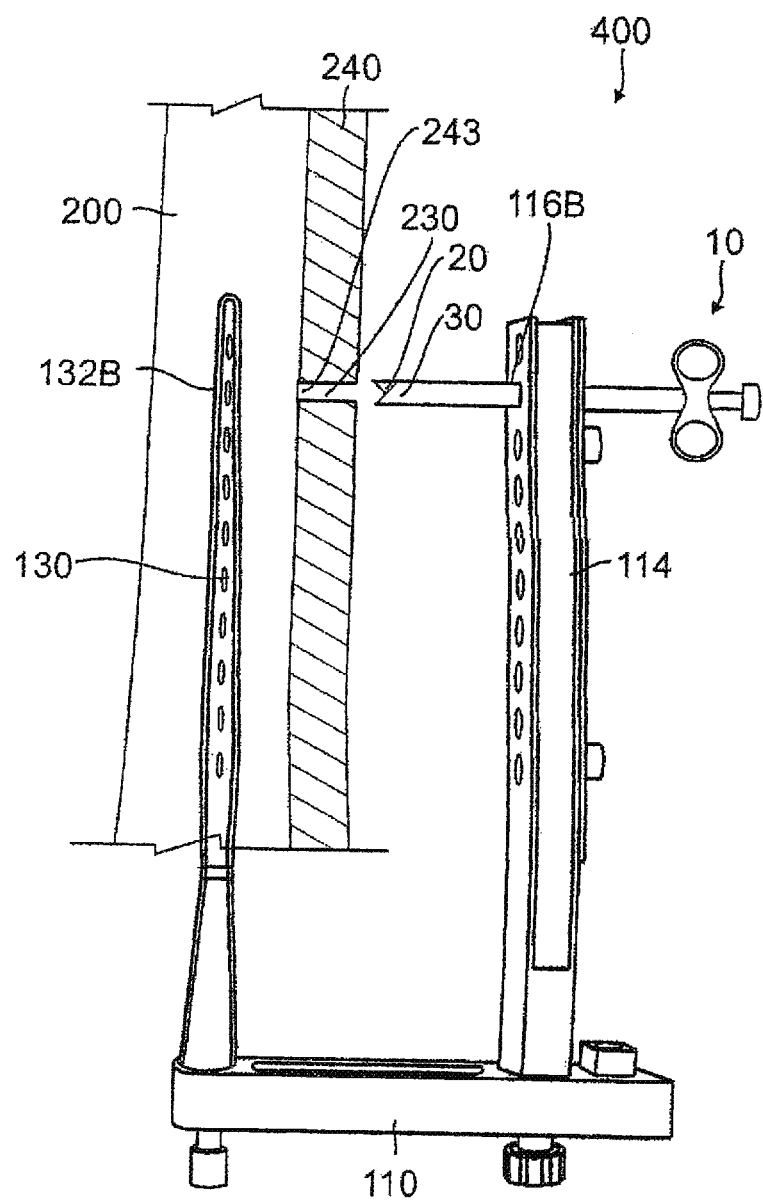
FIG. 15 is an illustration, not to scale, of a partial cross-section of a bone covered with skin and soft tissues with the locking nail inserted into the bone and a perspective view of the aligned targeting guide in place with the present invention scalpel instrument inserted through a targeting guide tunnel in the step after FIG. 14 and scalpel instrument removed from the skin and soft-tissue, and leaving a perfectly aligned tunnel in the skin and soft tissues.

FIG. 15 is the next step in the method 400, illustrating a partial cross-section of a bone 200 covered with skin and soft-tissue 240 with the locking nail 130 inserted into the bone 200 and a perspective view of the aligned targeting guide 114 in place with the present invention scalpel instrument 10 inserted through a targeting guide tunnel 116B in the targeting guide 114 the blades 20 and 30, in concave V-shape retracted formation, removed from the skin and soft-tissue 240, thereby creating a soft-tissue tunnel 230 that ends in a straight-line incision 243 at the bone 200. It can be seen that the soft-tissue tunnel 230 made by the present invention method 400 and apparatus 10, is in exact alignment with the screw hole 132B and the targeting guide tunnel 116B. It can further be seen that the straight-line incision 243 of the soft-tissue tunnel has been made with minimal trauma and minimal damage to the soft-tissue and deep fascia 240. It can further be seen that the soft-tissue tunnel 230 has not been made free hand, or by chance, but was carefully and precisely guided by the present invention method 400 using the present invention scalpel 10. It can further be seen that the present invention method 400 and apparatus 10 creates a soft-tissue tunnel 230 far more quickly, and yet still exceedingly precisely, than prior art methods and scalpels.

Figure 16:
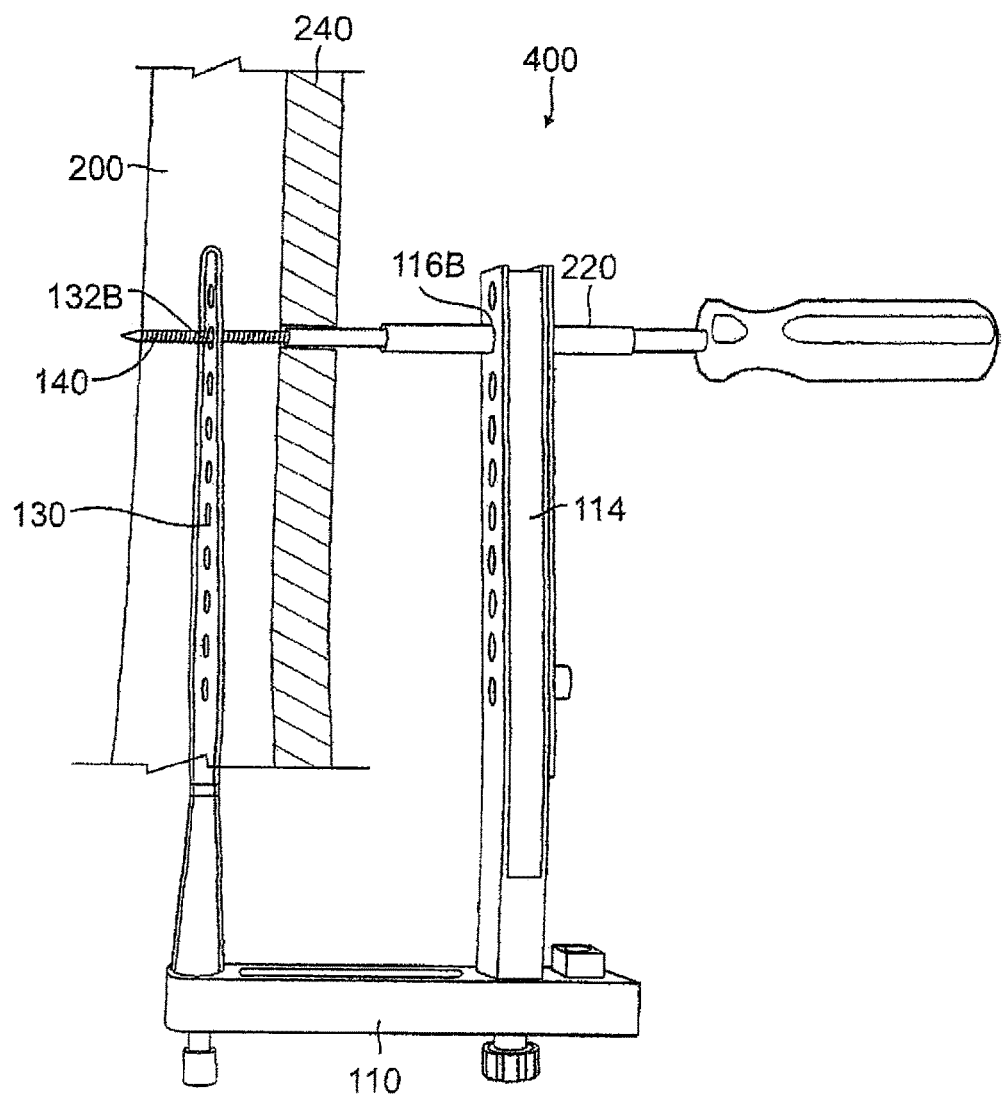
FIG. 16 is an illustration, not to scale, of a partial cross-section of a bone covered with skin and soft tissues with the locking nail inserted into the bone and a perspective view of the aligned targeting guide in place with the screw guide sleeve inserted through the opening in the skin and soft tissues left by the present invention and a screw driver inserting an affixing screw which passes through an opening in the locking nail within the bone.

FIG. 16 is the next step in the method 400, illustrating a partial cross-section of a bone 200 covered with skin and soft-tissue 240 with the locking nail 130 inserted into the bone 200 and a perspective view of the aligned targeting guide114 in place with the screw guide sleeve 220, in the targeting guide tunnel 116B. The scalpel 10 of the present invention has been removed from the targeting tunnel 116B and the method 400 of the present invention continues by inserting the screw guide sleeve 220 into the skin and soft-tissue tunnel 230 that ends at the bone. When the screw guide sleeve 220 reaches the bone 200, a screw 140 is guided through the screw guide sleeve 220 and surgically inserted with a screw driver 804 through the bone 200 and through a screw hole 132B in the locking nail 130, which corresponds with targeting guide tunnel 116B.

Figure 17:
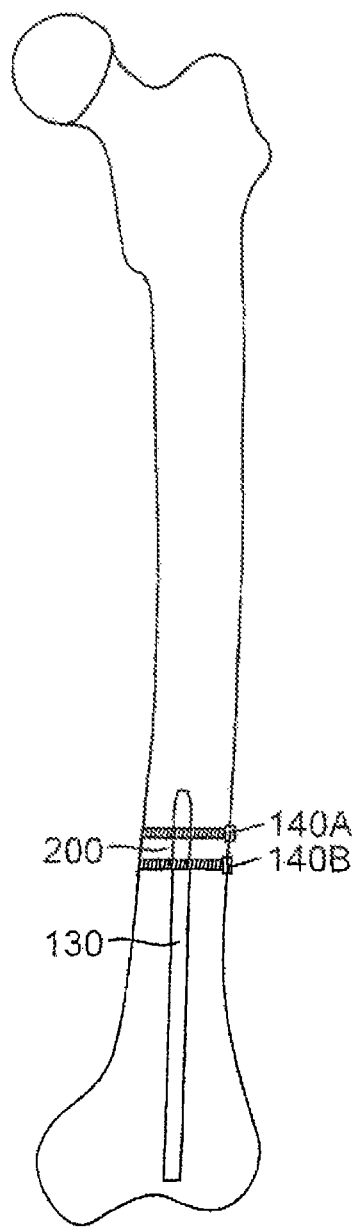
FIG. 17 is an illustration of the bone after the use of the method and apparatus of the present invention has been utilized and two screws are properly and precisely affixed at the correct angles to the bone, and through holes in the locking nail.

FIG. 17 is the next step in the method 400, illustrating the bone 200 after the use of the method 400 and apparatus 10 of the present invention has been utilized. It can be seen that the locking nail 130 remains in place in the bone 200 and that two screws 140A, 140B, have been properly and precisely affixed at the correct angles to the bone 200.

Described even more broadly, the present invention is a scalpel, comprising: (a) one mobile blade configured in such a way that its narrowest dimension is the same as, or narrower than, the width of a scalpel barrel, while the widest dimension of the blade is sufficiently wider than the width of the barrel to make an incision in skin; (b) the blade is set in such a way that it does not protrude radially outside the profile of the scalpel barrel in the contracted position; and (c) the blade is designed to create an incision of a given width by protruding beyond the radius of the barrel by a mechanism that rotates the blade 90 degrees so that by rotating the blade 90 degrees after passage through a targeting guide tunnel, a wider dimension protrudes radially from the sides of the barrel, and thereby presents a cutting edge that is wider than the scalpel barrel.

Of course the present invention is not intended to be restricted to any particular form or arrangement, or any specific embodiment, or any specific use, disclosed herein, since the same may be modified in various particulars or relations without departing from the spirit or scope of the claimed invention herein above shown and described of which the apparatus or method shown is intended only for illustration and disclosure of an operative embodiment and not to show all of the various forms or modifications in which this invention might be embodied or operated.

What is claimed is:

1. A surgical tool in combination with a targeting guide:
  a. said surgical tool comprising an elongated housing with first and second ends and defining an outer diameter, an actuation mechanism having a first end adjacent to the first end of the elongated housing, the first end of the actuation mechanism is within the elongated housing, a first blade with a first cutting edge, a second blade with a second cutting edge, each of the blades being movably connected to the first end of the actuation mechanism adjacent to the first end of the housing, the second end of said actuation mechanism movably connected to the second end of said housing wherein movement of the actuation mechanism moves the blades between a rest scissors position and a scalpel position, when the blades are in the rest scissors position, a portion of each of the first and second cutting edges are inwardly spaced to define a gap and the movement from the rest scissors position to the scalpel position allows the cutting edges to cooperate and perform scissors cutting on a work piece located in the gap, and when the blades are in the scalpel position the cuttings edges cooperate and form a single outer scalpel cutting edge, and when the blades are in the rest scissors position, the blades do not extend beyond the outer diameter of the housing, and when the blades are in the scalpel position, the blades extend beyond the outer diameter of the housing;

b. said targeting guide comprising a body including a multiplicity of aligned tunnels, each of the aligned tunnels extending through a thickness of the targeting guide body, each of the aligned tunnels having a front end and a rear end and a diameter larger than said outer diameter of said elongated housing of said surgical tool; and c. when said surgical tool is aligned with a respective one of said tunnels, at least the front end of the elongated housing with the blades in the scissors position passes through the front end and through the rear end of the respective one of said tunnels, and after the front end of the elongated housing has passed through the rear end of the respective one of said tunnels, the blades are moved to the scalpel position.

* * * * *